United States Patent

Chen et al.

[11] Patent Number: 5,458,887
[45] Date of Patent: Oct. 17, 1995

[54] CONTROLLED RELEASE TABLET FORMULATION

[75] Inventors: Chih-Ming Chen; Charles S. L. Chiao, both of Cooper City; José Suaréz, Miami, all of Fla.

[73] Assignee: Andrx Pharmaceuticals, Inc., Fort Lauderdale, Fla.

[21] Appl. No.: 24,825

[22] Filed: Mar. 2, 1994

[51] Int. Cl.⁶ .................................. A61K 9/22; A61K 9/30
[52] U.S. Cl. .......................... 424/464; 424/473; 424/479; 424/480; 424/481
[58] Field of Search ..................... 424/464, 473, 424/480, 482

[56] References Cited

U.S. PATENT DOCUMENTS

| | | | |
|---|---|---|---|
| 3,977,404 | 8/1976 | Theeuwes | 128/260 |
| 4,572,833 | 2/1986 | Pedersen et al. | 424/20 |
| 4,629,620 | 12/1986 | Lindahl et al. | 424/15 |
| 4,687,660 | 8/1987 | Baker et al. | 424/465 |
| 4,832,955 | 5/1989 | Snipes et al. | 424/456 |
| 4,880,830 | 11/1989 | Rhodes | 424/470 |
| 4,882,169 | 11/1989 | Ventouras | 424/493 |
| 4,892,742 | 1/1990 | Shah | 424/480 |
| 4,946,686 | 8/1990 | McClelland et al. | 424/473 |
| 5,026,560 | 6/1991 | Makino et al. | 424/494 |
| 5,051,262 | 9/1991 | Panoz et al. | 424/468 |
| 5,120,548 | 6/1992 | McClelland et al. | 424/473 |

Primary Examiner—Thurman K. Page
Assistant Examiner—James M. Spear
Attorney, Agent, or Firm—Hedman, Gibson & Costigan

[57] ABSTRACT

The present invention is directed to a controlled release dosage form which may be made using an osmotic core which contains a drug containing phase which includes a water swellable component and a continuous coating which comprises a major amount of a water resistant polymer and a minor amount of a non-toxic, water soluble, pharmaceutically acceptable compound.

14 Claims, 1 Drawing Sheet

CONTROLLED RELEASE TABLET FORMULATION

BACKGROUND OF THE INVENTION

The present invention is concerned with a controlled release tablet dosage formulation that is based on the use of a tablet core which has a coating which contains a major amount of a water insoluble polymer and a minor amount of a water soluble compound.

In order to provide a controlled release product, a water insoluble material such as a resin or a wax has been used to coat discrete drug containing units in order to resist the action of the fluids in the gastrointestinal tract. These coatings have resulted in the production of satisfactory pellets or granules that would usually be placed in a gelatin capsule because if a tablet was made from the resin or wax coated pellets, the coating would either rupture or become so deformed that the uniformity of any wax coating would be adversely affected.

U.S. Pat. No. 3,977,404 discloses that in the prior art, attempts were made to make sustained release devices by placing a water soluble drug in a polymer film and allowing the drug to be leached out. Another attempt was based on the use of a drug that was coated with a film of water insoluble plastic containing a modifying agent which was soluble at a certain pH. This device would form a porous film under the proper pH conditions which would allow gastrointestinal fluid to dissolve the drug and leach it outwards through the pores in the film. The pH dependent nature of the film made it difficult to control the rate and site of release because of variations in the pH of the gastrointestinal tract.

Osmotic tablets are described in U.S. Pat. No. 3,977,404 which are based on the use of a microporous core which is coated with a material that does not allow for the passage of a drug. These tablets are provided with a pre formed osmotic delivery orifice which allows gastrointestinal fluid to flow into the osmotic core and cause the osmotic core to deliver the contents of the core over an extended period of time. Other variations on this concept are described in U.S. Pat. No. 4,687,660 which describes the use of a polymer coating having a water soluble pore forming material therein which surrounds a core which contains a water soluble enhancing agent.

SUMMARY OF THE INVENTION

The present invention is directed to a controlled release dosage form which may be made using an osmotic core which contains a drug containing phase which includes a water swellable component and a continuous coating which comprises a major amount of a water resistant polymer and a minor amount of a non-toxic, water soluble, pharmaceutically acceptable compound.

Accordingly it is a primary object of this invention to provide a novel controlled release dosage formulation.

It is also an object of this invention to provide a novel tabletted formulation which is made by forming a core which contains a drug and a water swellable agent and coating said core with a continuous coating which comprises a polymer and a water soluble compound.

It is also an object of this invention to provide an osmotic tablet which does not require a pre-formed osmotic delivery orifice which exposes the osmotic core to the action of gastrointestinal fluid.

It is also an object of this invention to provide a novel osmotic tablet in which the osmotic core is sealed against the ambient atmosphere.

These and other objects of the invention will become apparent from a review of the appended specification.

DETAILED DESCRIPTION OF THE INVENTION

Figure 1:
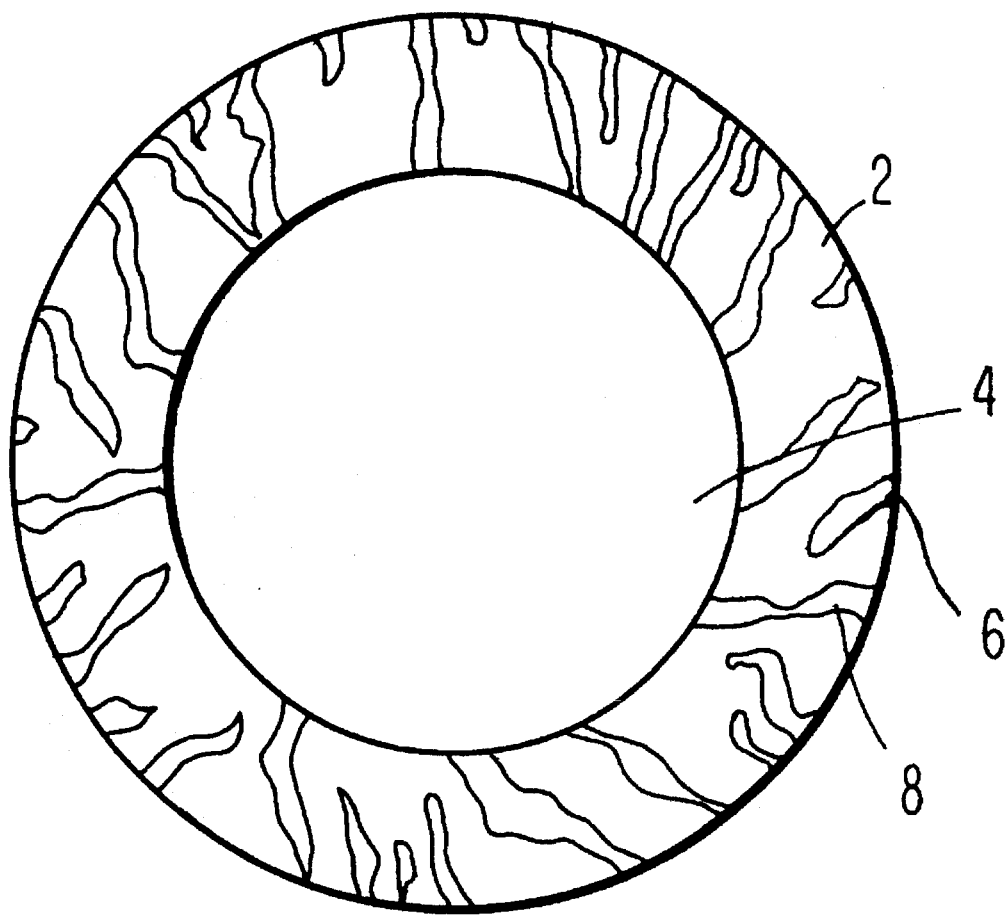
FIG. 1 is a cross-sectional schematic view of an osmotic tablet according to the invention which has been exposed to an aqueous environment for a sufficient period of time to dissolve out non-toxic, water soluble, pharmaceutically acceptable compound from the continuous water resistant polymer membrane and provide multiple access channels which expose the osmotic core to the action of gastrointestinal fluids.

The present invention is directed to a controlled release dosage form which may be made using an osmotic core which contains a drug containing phase and a swelling agent and optionally an osmotic flow agent. The swelling agent is a water insoluble hydrophilic material which may be hydroxypropylmethyl cellulose or polyethylene oxide. The purpose of the swelling agent is to expand the core and provide a drug rich surface in contact with the internal end of the microporous channels that are formed when the non-toxic, water soluble, pharmaceutically acceptable compound dissolves in the gastrointestinal fluid. The presence of a drug rich surface in contact with the interior of the water insoluble polymer provides for a substantially continuous availability of drug which is transported through the microporous channels of the water insoluble polymer.

The osmotic agent which is optionally placed in the tablet core is an agent which is water soluble and will provide an osmotic pressure in the tablet which is greater than the osmotic pressure in the gastrointestinal fluid. The presence of the osmotic agent will enhance the delivery of the drug from the core of the coated tablet of the invention. Suitable osmotic agents include magnesium sulfate, magnesium chloride, sodium chloride, lithium chloride, potassium sulfate, sodium carbonate, lithium sulfate, potassium chloride, calcium bicarbonate, sodium sulfate, calcium lactate, potassium acid phosphate, urea, magnesium succinate, sucrose, citric acid, or mixtures thereof and the like. The swelling agent is used in an amount which will result in the expansion of the tablet core without causing the tablet to rupture as the swelling agent becomes wet with gastrointestinal fluid. The osmotic agent is used in an amount which will result in an increased osmotic pressure between the core of the tablet and the gastrointestinal fluid which contacts the tablet in vivo. The tablet core may comprise from 40 to 90 wt % and preferably 65 to 85 wt % of the drug; from 0.5 to 15 wt % and preferably 2 to 8 wt % of the swelling agent and optionally from 0.5 to 15 wt % and preferably 2 to 8% of the osmotic agent. The wt % is computed based on the total weight of the drug, swelling agent and osmotic agent.

The water resistant polymer may be any polymer which forms a semi-permeable membrane that has a water sorptivity of 5 to 50% by weight. The materials from which the water resistant polymer may be made include cellulose acetate, cellulose triacetate, agar acetate, amylose triacetate, beta glucan acetate, acetaldehyde dimethyl acetate, cellulose acetate methyl carbamate, cellulose acetate phthalate, cellulose acetate succinate, cellulose acetate dimethylamino acetate, cellulose acetate ethyl carbonate, cellulose acetate chloroacetate, cellulose acetate ethyl oxalate, cellulose acetate propionate, poly(vinylmethylether) copolymers, cellulose acetate butyl sulfonate, cellulose acetate octate, cellulose acetate laurate, cellulose acetate p-toluene sulfonate, triacetate of locust gum bean, hydroxylated ethylene-vinyl acetate, cellulose acetate butyrate, ethyl cellulose and the like. Other useful membrane forming materials are disclosed in U.S. Pat. No. 3,977,404, which is incorporated by reference.

The non-toxic, water soluble, pharmaceutically acceptable material may be selected from magnesium sulfate, magnesium chloride, sodium chloride, lithium chloride, potassium sulfate, sodium carbonate, lithium sulfate, potassium chloride, calcium bicarbonate, sodium sulfate, calcium lactate, potassium acid phosphate, urea, magnesium succinate, sucrose, citric acid, or mixtures thereof and the like.

Generally, the ratio of the water resistant polymer to the non-toxic, water soluble, pharmaceutically acceptable material will be 20:1 to 2:1, and preferably about 8:1 to 4:1.

The drug that may be formulated according to the method of the present invention may be any inorganic or organic medicinal including but not limited to antibiotics, tranquilizers, agents which act on the heart, liver, kidneys, central nervous system, muscles, contraceptives, hormonal agents, antineoplastic agents or combinations of therapeutically complimentary drugs. These drugs are described in the Physicians Desk Reference, 1993 Ed., and U.S. Pat. No. 3,977,404 which are incorporated by reference. The preferred drugs are water soluble drugs.

The amount of the drug is that amount which is sufficient to deliver a therapeutic plasma level which is sufficient to provide the desired therapeutic result. The dosages for the drugs which are usable according to the present invention are described in the literature and one who is skilled in the art can readily determine the amount of any particular drug which is to be used by routine experimentation.

The following Example is merely added to illustrate the invention and is not to be considered as limiting the scope of the invention in any way.

EXAMPLE

A core tablet was prepared which had the following formulation:

| | |
|---|---|
| Pseudoephedrine HCl, U.S.P. | 79.34 wt % |
| Povidone, U.S.P. (Kollidon K30) | 9.4 wt % |
| Polyethylene oxide | 5.24 wt % |
| Sodium Chloride, U.S.P. | 3.00 wt % |
| Myvatex, Eastman Kodak (lubricant) | 3.00 wt % |

The pseudoephedrine HCl is granulated in the solution of povidone in a fluid bed processor. The granulated product is is combined with the polyethylene oxide and the sodium chloride in a Patterson Kelly blender at 25 rpm for 10 minutes. The Myvatex is passed through a #40 US Standard mesh screen and added to the blender. The combined ingredients are blended for an additional 3 minutes. The powder blend is compressed into tablets using a punch tip size of 0.375" in diameter; a weight of 242 mg (230–254 mg.) and a hardness of 10–20 kp.

A sustained release coating composition is prepared using the following formulation:

| | |
|---|---|
| Cellulose Acetate (Wt Av MW 30,000) | 7.35 wt % |
| Sodium Chloride | 1.47 wt % |
| Triacetin | 2.12 wt % |
| Acetone | 40.0 wt % |

The cellulose acetate is dissolved in the acetone in a stainless steel tank using a propeller shaped stirring device. The triacetin is then added and the sodium chloride is then dispersed in the solution. The previously prepared pseudoephedrine tablets are spray coated in a fluidized bed coater with the coating suspension to provide coated tablets which have a coating which is 11% by weight of the total weight of the uncoated tablets and the coating. These tablets release the pseudoephedrine HCl over a period of 24 hours when 500 ml of purified water was used as the dissolution medium and the USP XXII paddle method at 100 rpm.

We claim:

1. A controlled release dosage pharmaceutical tablet which comprises:

(a) an osmotic core which consists essentially of a drug and a water swellable component selected from the group consisting of hydroxypropylmethyl cellulose and polyethylene oxide in admixture with said drug; and (b) a coating which comprises a water resistant polymer and a minor amount of a non-toxic, water soluble, pharmaceutically acceptable compound in an amount which is sufficient to dissolve in gastrointestinal fluid and form a plurality of micropores in the outside of said tablet said water resistant polymer which are microporous to the passage of gastrointestinal fluid.

2. A controlled release dosage pharmaceutical tablet which comprises:

(a) an osmotic core which consists essentially of a drug, a water swellable component selected from the group consisting of hydroxypropylmethyl cellulose and polyethylene oxide in admixture with said drug, an osmotic agent; and (b) a coating which comprises a water resistant polymer and a minor amount of a non-toxic, water soluble, pharmaceutically acceptable compound in an amount which is sufficient to dissolve in gastrointestinal fluid and form a plurality of micropores in the outside of said tablet said water resistant polymer which are microporous to the passage of gastrointestinal fluid.

3. A controlled release pharmaceutical dosage tablet which comprises:

(a) an osmotic core which consists essentially of a drug in admixture with, an osmotic amount of sodium chloride and as a swellable component polyethylene oxide; and (b) a coating which comprises a cellulose acetate, triacetin and a minor amount of sodium chloride in an amount which is sufficient to dissolve in gastrointestinal fluid and form a plurality of micropores in the outside of said tablet which render said water resistant polymer microporous to the passage of gastrointestinal fluid.

4. A pharmaceutical controlled release dosage tablet as defined in claim 2 wherein the ratio of the water resistant polymer to the non-toxic, water soluble, pharmaceutically acceptable material is from 20:1 to 2:1.

5. A pharmaceutical controlled release dosage tablet as defined in claim 4 wherein the ratio of the water resistant polymer to the non-toxic, water soluble, pharmaceutically acceptable material is from 8:1 to 4:1.

6. A pharmaceutical controlled release dosage tablet as defined in claim 5 wherein the tablet core contains from to 0.5 to 15 wt % of the swelling agent.

7. A pharmaceutical controlled release dosage tablet as defined in claim 5 wherein the tablet core contains from to 0.5 to 15 wt % of an osmotic agent.

8. A pharmaceutical controlled release dosage tablet as defined in claim 5 wherein the polymer in the coating which comprises a water resistant polymer is selected from the group consisting of cellulose acetate, cellulose triacetate, agar acetate, amylose triacetate, beta glucan acetate, acetaldehyde dimethyl acetate, cellulose acetate methyl carbamate, cellulose acetate phthalate, cellulose acetate succinate, cellulose acetate dimethylamino acetate, cellulose acetate ethyl carbonate, cellulose acetate chloroacetate, cellulose acetate ethyl oxalate, cellulose acetate butyl sulfonate, cellulose acetate propionate, poly(vinylmethylether) copolymers, cellulose acetate butyl sulfonate, cellulose acetate octate, cellulose acetate laurate, cellulose acetate p-toluene sulfonate, triacetate of locust gum bean, hydroxylated ethylene-vinyl acetate, cellulose acetate butyrate and ethyl cellulose.

9. A pharmaceutical controlled release dosage tablet as defined in claim 8 wherein the polymer in the coating which comprises a water resistant polymer is cellulose acetate.

10. A pharmaceutical controlled release dosage tablet as defined in claim 5 wherein the non-toxic, water soluble, pharmaceutically acceptable compound is selected from the group consisting of magnesium sulfate, magnesium chloride, sodium chloride, lithium chloride, potassium sulfate, sodium carbonate, lithium sulfate, potassium chloride, calcium bicarbonate, sodium sulfate, calcium lactate, potassium acid phosphate, urea, magnesium succinate,sucrose, citric acid and mixtures thereof.

11. A pharmaceutical controlled release dosage tablet as defined in claim 8 wherein the osmotic agent is selected from the group consisting of magnesium sulfate, magnesium chloride, sodium chloride, lithium chloride, potassium sulfate, sodium carbonate, lithium sulfate, potassium chloride, calcium bicarbonate, sodium sulfate, calcium lactate, potassium acid phosphate, urea, magnesium succinate, sucrose, citric acid and mixtures thereof.

12. A pharmaceutical controlled release dosage tablet as defined in claim 1 wherein the polymer in the coating which comprises a water resistant polymer includes a plasticizer.

13. A controlled release pharmaceutical dosage tablet as defined in claim 3 which consists essentially of:
  (a) an osmotic core which consists essentially of a drug in admixture with, an osmotic amount of uncoated sodium chloride and as a swellable component polyethylene oxide; and
  (b) a coating which comprises a cellulose acetate, triacetin and a minor amount of sodium chloride in an amount which is sufficient to dissolve in gastrointestinal fluid and form a plurality of micropores to the outside of said tablet which render said water resistant polymer microporous to the passage of gastrointestinal fluid.

14. A controlled release dosage pharmaceutical tablet which consists essentially of:
  (a) an osmotic core which consists of a drug and a water swellable component selected from the group consisting of hydroxypropylmethyl cellulose and polyethylene oxide in admixture with said drug; and
  (b) a coating which comprises a water resistant polymer and a minor amount of a non-toxic, water soluble, pharmaceutically acceptable compound in an amount which is sufficient to dissolve in gastrointestinal fluid and form a plurality of micropores in the outside of said tablet said water resistant polymer which are microporous to the passage of gastrointestinal fluid.

* * * * *